United States Patent [19]

Gradeff et al.

[11] Patent Number: 5,017,694

[45] Date of Patent: * May 21, 1991

[54] PROCESS FOR THE PREPARATION OF CERIC HYDROCARBYL SILYLOXIDES BY TRANSETHERIFICATION OF CERIC ALKOXIDES

[75] Inventors: Peter S. Gradeff, Pottersville; Kenan Yunlu, Highland Park, both of N.J.

[73] Assignee: Rhone-Poulenc, Inc., New Brunswick, N.J.

[*] Notice: The portion of the term of this patent subsequent to Sep. 21, 2006 has been disclaimed.

[21] Appl. No.: 128,248

[22] Filed: Dec. 3, 1987

[51] Int. Cl.$^5$ ............................................. C07F 5/00
[52] U.S. Cl. ................................................... 534/15
[58] Field of Search ......................................... 534/15

[56] References Cited

U.S. PATENT DOCUMENTS 3,267,036  8/1964  Baker et al. ...................... 252/49.7
3,884,950  5/1975  Koda et al. .................... 252/49.7 X
4,070,343  12/1978  Kishimoto et al. ............. 252/49.7 X
4,489,000  12/1984  Gradeff et al. .................... 260/429.2
4,663,439  5/1987  Gradeff et al. .................... 534/15 X

OTHER PUBLICATIONS

Rad'Kov et al., *Journal of the General Chemistry of the U.S.S.R.*, (1986), pp. 336–338.

Batwara et al., *Journal of Inorganic Nuclear Chemistry*, (1970), pp. 411–415.

*Primary Examiner*—John S. Maples
*Assistant Examiner*—Cynthia Harris

[57] ABSTRACT

A process is provided for preparing ceric hydrocarbyl silyloxides, which comprises transetherifying a ceric alkoxide with the silanol having the desired hydrocarbyl group and the desired number of hydroxyl groups under anhydrous conditions at a temperature within the range from about −30° C. to about 200° C., thereby displacing the aliphatic alcohol of the alkoxide and forming the ceric hydrocarbyl silyloxide of the silanol.

15 Claims, No Drawings

PROCESS FOR THE PREPARATION OF CERIC HYDROCARBYL SILYLOXIDES BY TRANSETHERIFICATION OF CERIC ALKOXIDES

Polyvalent metal alkoxides are an important class of versatile organometallic compounds that have many industrial uses. In some instances their uses parallel the metal carboxylates and other organometallic compounds, but they have advantages over such compounds because of their catalytic properties, ease of hydrolysis, solubility in organic solvents, and volatility. They have been used as paint additives, water repellents, adhesion promoters, mordants, sizing agents in enamel compositions, catalysts and also very importantly as intermediates in synthesis of other organic compounds.

There are four general preparative methods for metal alkoxides, all under anhydrous conditions, as follows:

A. By reaction of the corresponding alcohol and metal, such as the alkali metals, alkaline earth metals, and aluminum, with the assistance of an alkaline or acidic catalyst.

B. By reaction of the corresponding alcohol with the oxides and hydroxides of the metal, for instance NaOH or $Na_2O$, $V_2O_5$ and $MoO_3 \cdot 2H_2O$.

C. By reaction of the corresponding alcohol and metal halide in the presence of an anhydrous base. A typical example is the preparation of $Th(OR)_4$ or $Zr(OR)_4$:

$$ThCl_4 + 4ROH + 4NaOR \rightarrow Th(OR)_4 + 4NaCl$$

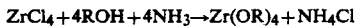

$$ZrCl_4 + 4ROH + 4NH_3 \rightarrow Zr(OR)_4 + NH_4Cl$$

The reaction can be used for preparing alkoxides of titanium, hafnium, germanium, niobium, tantalum, aluminum and tin.

D. By transetherification of the metal alkoxides of lower alcohols, such as the methoxides, ethoxides or isopropoxides, with a higher alcohol.

Method A is exemplified for a number of yttrium, lanthanum and other lanthanide alkoxides by L. Brown and K. Mazdiyasni in *Inorganic Chemistry*, (1970) 2783. The reaction, previously thought to be useful only for the alkali metals, magnesium and aluminum, was extended by them to the synthesis of yttrium and all of the lanthanide, isopropoxides. For the lower lanthanides, such as lanthanum, cerium, praesodymium and neodymium, a mixture of $HgCl_2$ and $Hg(C_2H_3O_2)_2$ or $HgI_2$ is used as a catalyst, to increase both the rate of reaction and percent yield. Generally, 5 g of metal turnings is reacted with about 300 ml of isopropyl alcohol at reflux temperature for about 24 hours and in the presence of a small amount of Hg salt catalyst. The yields are said to be 75% or better.

Most of the other examples in the literature of the pre preparation of alkoxides of lanthanides refer to the use of the corresponding metal halides. In some cases, a complex $LaCl_3 \cdot 3ROH$ is preferred to the $LaCl_3$ (Misra et al, *Austr. J. Chem.* 21 797 (1978) and Mehrotra and Batwara, *Inorganic Chem.* 9 2505 (1970)).

An interesting variation of Method D is mentioned by Tripathi, Batwara, and Mehrotra *J.C.S.A.* 1967 991. Lower ytterbium alkoxides (such as the methoxide and ethoxide) were synthesized from ytterbium isopropoxide, by transetherification with methanol or ethanol. Owing to their sparing solubility, these alcohols were removed by precipitation as the reaction proceeded, driving the transetherification to completion.

In general, Methods A, B and C are only suited for preparation of the lower alkoxides, such as the methoxides, ethoxides and isopropoxides, since the reactivity of higher alcohols diminishes with increase in their molecular weights. The higher alkoxides are better prepared by Method D, which is a two-step process.

The only published method for preparing ceric alkoxides applied Method C to ceric chloride, Bradley et al, *J.C.S.* 1956 2260–64. Since cerium tetrachloride is unstable, the dipyridinium cerium hexachloride complex was Bradley et al's choice as starting material.

Cerium dioxide was first converted to ceric ammonium sulphate. Pure ceric hydroxide was precipitated from an aqueous solution of ceric ammonium sulphate and washed thoroughly. The freshly-prepared ceric hydroxide, suspended in absolute alcohol, was treated with anhydrous hydrogen chloride and then pyridine was added, which formed the insoluble dipyridinium cerium hexachloride complex $(Py)_2CeCl_6$. The complex was filtered, dried, and used for preparing the methoxide, ethoxide and isopropoxide directly, while the propyl, butyl, secondary butyl, neopentyl and n-pentyl alkoxides were made by alcohol interchange, i.e., transetherification, from the isopropoxide. The methoxide and ethoxide were also made by exchange from the isopropoxide.

Gradeff and Schreiber, U.S. Pat. No. 4,489,000, patented Dec. 18, 1984, provide a process for preparing ceric alkoxides which comprises reacting ceric ammonium nitrate with an alcohol under anhydrous conditions in the presence of an anhydrous base at a temperature within the range from about $-30°$ C. to about $200°$ C., preferably from about $0°$ C. to about $150°$ C., until ceric alkoxide and the nitrate salt of the base are formed.

This process avoids the necessity described by Bradley et al of first preparing the ceric hydroxide from the ceric salt, in their case, ceric ammonium sulphate, and converting the hydroxide subsequently to the chloride, which needs to be stabilized as the pyridine complex.

It is rather surprising, despite the considerable volume of work done on the preparation of rare earth metal silicon compounds, that cerium hydrocarbyl silyloxides are unknown, as well as a suitable process for preparing them.

Bradley and Thomas, *J. Chem. Soc.* 1959 3404 have reported work on alkyl silyloxy derivatives of titanium, zirconium, neobium and tantalum, using trimethyl silanolysis of titanium or zirconium isopropoxides, or using trialkyl silyl acetate in place of the silanol, but there is no reference to cerium.

Bradley and Prevedorou-Demas, *J. Chem. Soc.* 1964 1580 reported further work on zirconium oxide trimethyl silyloxide polymers.

In neither paper is there reference to cerium silyloxides.

In accordance with the present invention, a process is provided for preparing ceric hydrocarbyl silyloxides which comprises transetherifying a ceric alkoxide with the silanol having the desired hydrocarbyl group and the desired number of hydroxyl groups under anhydrous conditions at a temperature within the range from about $-30°$ C. to about $200°$ C., thereby displacing the aliphatic alcohol of the alkoxide and forming the ceric hydrocarbyl silyloxide of the silanol. The ceric hydrocarbyl silyloxides can be isolated pure or as complexes with the solvent; in some cases, the silyloxide can be used without separation from the reaction mixture.

Cerium alkoxides are thought to exist in the form of the alkoxide and as association complexes with free alcohol, and since these appear to be unstable, as decomposition products thereof. All of these are included in what is commonly referred to as "cerium alkoxide", and so the term is used here in this commonly accepted sense.

The product, a ceric hydrocarbyl silyloxide, is believed to be novel, since it has not previously been reported in the literature, and is characterized by one or more groups having a tetravalent cerium linked via oxygen to one, two, three or four silicon atoms, as shown, the remaining three or two, respectively, valences of the silicon being linked to hydrocarbyl groups having from one to about ten carbon atoms. The compounds can have one, two, three or four silicon atoms, in a single unit, or in a plurality of such units linked in linear, branched or cage-type oligomers or polymers, when the starting silanol is a diol.

Accordingly, the ceric hydrocarbyl silyloxides can be defined by the following general formula:

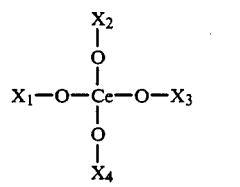  I where $OX_1$, $OX_2$, $OX_3$ and $OX_4$ are selected from the group consisting of $OR_1$, $NO_3$ and $[O]_{4-y}SiR_y$; and any two of $X_1$ and $X_2$ and $X_3$ and $X_4$ can be taken together as $>SiR_y$; the number of $SiR_y$ can be 1, 2, 3 or 4 and y can be 1, 2 or 3.

When y=2, the silicon is linked to two of the oxygens as $>SiR_y$ in (1) the same or (2) a different cerium atom; in (1) the species are monomeric; in (2) they can be oligomers or polymers.

At least one of $X_1$, $X_2$, $X_3$ and $X_4$ is $O_{4-y}SiR_y$, at least one R is hydrocarbyl, and no more than one R may be hydrogen.

Examples of compounds falling within Formula I according to the value of $X_1$, $X_2$, $X_3$, $X_4$ include:

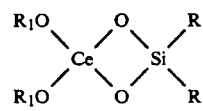  1.

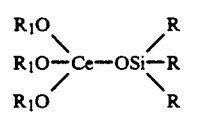  2.

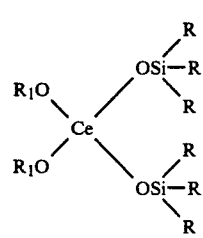  3.

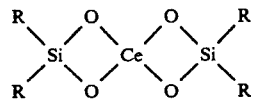  4.

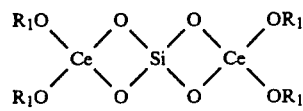  5.

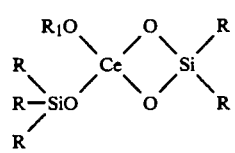  6.

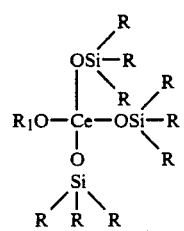  7.

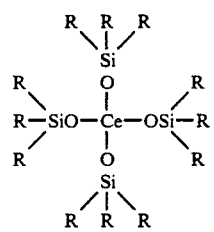  8.

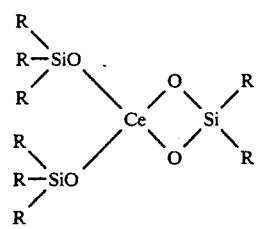  9.

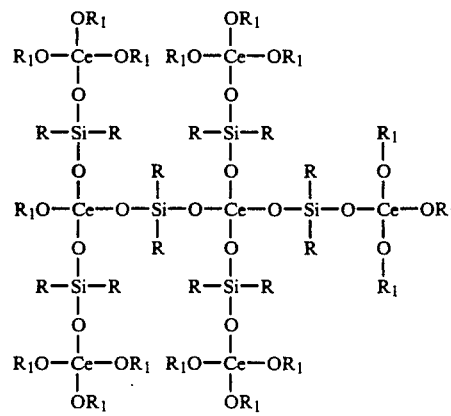  10.

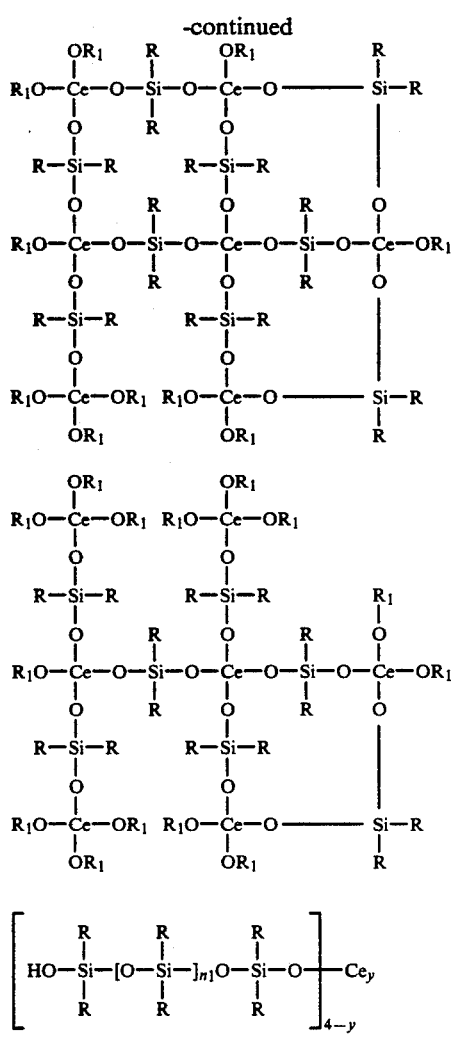

11.

12.

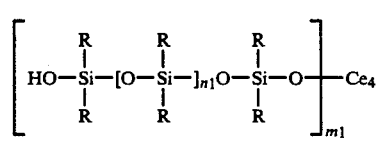

13.

wherein y is the number of cerium atoms in the polymer and can range from 1 to about 10.

14.

wherein $m_1$ is the number of such units in the polymer and can range from 1 to about 10.

R in the above formulae is hydrogen or a hydrocarbyl group having from one to about ten carbon atoms, and the R's attached to any silicon can be the same or different.

$R_1$ is a hydrocarbyl group attached via oxygen to cerium and having from one to about ten carbon atoms, and the $R_1$'s attached to any cerium can be the same or different.

Exemplary hydrocarbyl R and $R_1$ groups include alkyl, straight or branched alkenyl, cycloalkyl, cycloalkenyl, phenyl and alkyl phenyl, naphthyl and alkyl naphthyl groups.

Exemplary R and $R_1$ alkyl include methyl, ethyl, propyl, isopropyl, butyl, sec-butyl, hexyl, octyl, isooctyl, 2-ethylhexyl, nonyl and decyl.

Exemplary R and $R_1$ alkenyl include vinyl, allyl, butenyl, hexenyl, octenyl, nonenyl and decenyl.

Exemplary R and $R_1$ cycloalkyl include cyclopentyl, cyclohexyl, cycloheptyl and cyclooctyl; cyclopentenyl, cyclohexenyl and cycloheptenyl.

Exemplary R and $R_1$ alkaryl include phenyl, phenylmethyl, and phenylethyl.

The hydrocarbyl silanol can be any of several types:

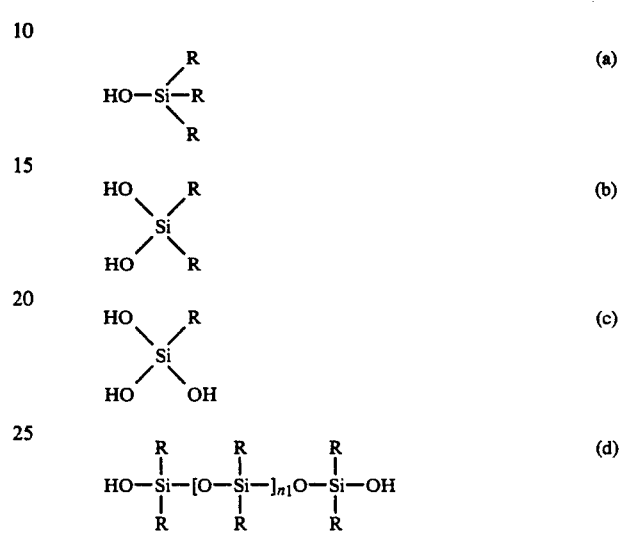

wherein $n_1$ is the number of such units in the polymer and can range from 1 to about 10.

Group (d) includes solid silicone resins containing free OH groups, which can be solubilized and used in the reaction with ceric ammonium nitrate to form silicone resin linked to cerium via the oxygen.

R is hydrogen or the hydrocarbyl group desired in the silyloxide product, and the R's attached to any silicon can be the same or different.

Preferred subclasses of silanols include:

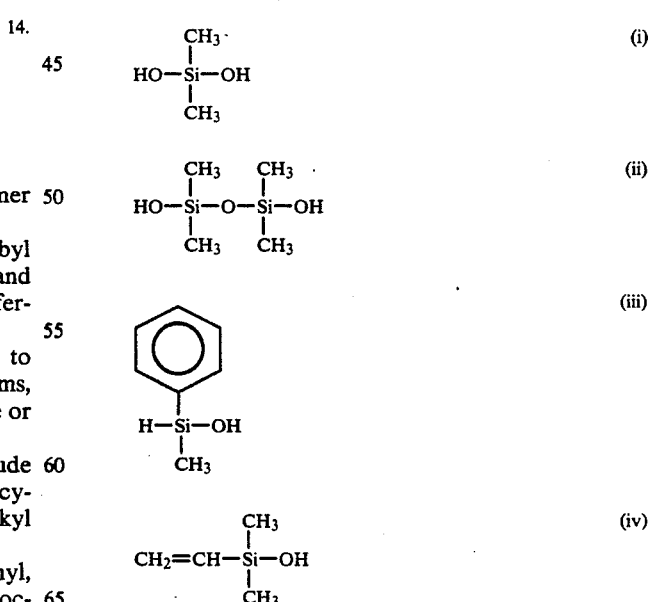

-continued

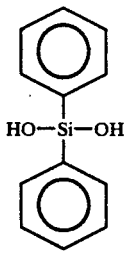
(vi)

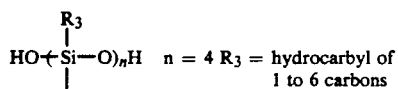
(vii)
n = 4  R₃ = hydrocarbyl of 1 to 6 carbons

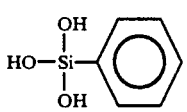
(viii)

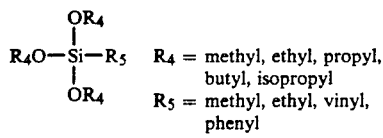
(ix)
R₄ = methyl, ethyl, propyl, butyl, isopropyl
R₅ = methyl, ethyl, vinyl, phenyl The process proceeds with ease with the lower aliphatic monohydric, dihydric and trihydric silanols having one, two or three hydrocarbyl groups of from one to six carbon atoms, for example, trimethyl silanol, triethyl silanol, tripropyl silanol, triisopropyl silanol, tributyl silanol, triisobutyl silanol, tri-sec-butyl silanol, tri-tert-butyl silanol, tripentyl silanol, triisopentyl silanol, tri-sec-pentyl silanol, tri-tert-pentyl silanol, and trihexyl silanol; dimethyl silanediol, diethyl silanediol, dipropyl silanediol, diisopropyl silanediol, dibutyl silanediol, diisobutyl silanediol, di-sec-butyl silanediol, di-tert-butyl silanediol, dipentyl silanediol, diisopentyl silanediol, di-sec-pentyl silanediol, di-tert-pentyl silanediol and dihexyl silanediol; methyl silanetriol, ethyl silanetriol, propyl silanetriol, isopropyl silanetriol, butyl silanetriol, isobutyl silanetriol, sec-butyl silanetriol, tert-butyl silanetriol, pentyl silanetriol, isopentyl silanetriol, sec-pentyl silanetriol, tert-pentyl silanetriol and hexyl silanetriol.

A higher aliphatic, cycloaliphatic or aromatic hydrocarbyl silanol having at least seven up to about twenty carbon atoms can be incorporated directly in the reaction mixture together with a lower aliphatic silanol having from one to six carbon atoms to form a ceric silyloxide of the higher silanol. Exemplary are triheptyl silanol, triisoheptyl silanol, trioctyl silanol, triisooctyl silanol, tri-2-ethyl-hexyl silanol, tri-sec-octyl silanol, tri-tert-octyl silanol, trinonyl silanol, triisonoyl silanol, tridecyl silanol, tridodecyl silanol, tritetradecyl silanol, trioctadecyl silanol, trihexadecyl silanol, trioleyl silanol, and trieicosyl silanol; or a cycloaliphatic silanol having from three to about twenty carbon atoms, such as for example tricyclopropyl silanol, tricyclobutyl silanol, tricyclopentyl silanol, tricyclohexyl silanol, tricycloheptyl silanol, tricyclooctyl silanol, tricyclododecyl silanol, tripropyl cyclohexyl silanol, trimethyl cyclohexyl silanol and trimethyl cycloheptyl silanol; or an aromatic or alkyl aromatic silanol having from seven to about twenty carbon atoms, such as for example, triphenyl silanol, tribenzyl silanol, triphenethyl silanol, triphenpropyl silanol, triphenoctadecyl silanol and trinaphthdecyl silanol; diheptyl silanediol, diisoheptyl silanediol, dioctyl silanediol, diisooctyl silanediol, di-2-ethyl-hexyl silanediol, di-sec-octyl silanediol, di-tert-octyl silanediol, dinonyl silanediol, diisononyl silanediol, didecyl silanediol, dicyclopropyl silanediol, dicyclobutyl silanediol, dicyclopentyl silanediol, dicyclohexyl silanediol, dicycloheptyl silanediol, dicyclooctyl silanediol, dipropyl cyclohexyl silanediol, dimethyl cyclohexyl silanediol and dimethyl cycloheptyl silanediol; diphenyl silanediol, dibenzyl silanediol, diphenethyl silanediol, diphenpropyl silanediol; heptyl silanetriol, isoheptyl silanetriol, octyl silanetriol, isooctyl silanetriol, 2-ethyl-hexyl silanetriol, sec-octyl silanetriol, tert-octyl silanetriol, nonyl silanetriol, isononyl silanetriol, decyl silanetriol, cyclopropyl silanetriol, cyclobutyl silanetriol, cyclopentyl silanetriol, cyclohexyl silanetriol, cycloheptyl silanetriol, cyclooctyl silanetriol, propyl cyclohexyl silanetriol, methyl cyclohexyl silanetriol and methyl cycloheptyl silanetriol; phenyl silanetriol, benzyl silanetriol, phenethyl silanetriol, phenpropyl silanetriol, naphthyl silanetriol (where too unstable, the triols are used in the form of their ethers).

The final reaction product is the ceric hydrocarbyl silyloxide of the higher silanol, but it is believed that the lower silanol expedites the reaction by first forming a silyloxide with the cerium, this silyloxide being converted by transetherification with the higher silanol to the silyloxide of the higher silanol.

The above-described reactions can be carried out in the presence of an excess of the silanol, which also can be a solvent for the corresponding silyloxide. Other inert solvents in addition to the reactant silanol may be needed in order to dissolve the ceric ammonium nitrate such as DME, or other glymers, THF or alcohols. Inert solvents also may be required to separate products from the nitrate by-products, for instance, pentane, benzene, toluene, pet. spirits etc. If desired, the solvent can be separated from the reaction product by distillation at atmospheric or reduced pressure, following completion of the reaction. It is understood that one or two molecules of a solvent such as DME for instance may remain coordinated to the cerium.

The reaction proceeds under anhydrous conditions at a temperature within the range from about −30° C. to about 200° C., preferably from about 0° C. to about 150° C., most preferably at room temperature, depending on the solvent system and base used.

The reaction does not require the presence of an anhydrous base, since the cerium alkoxide is itself a base, but, if desired, a base can be added. Exemplary are ammonia, or an alkali metal or ammonium alkoxide, silyloxide or polysiloxanoxide, desirably of the corresponding silanol, so as to avoid contamination of the silyloxide reaction product with another silyloxide.

Exemplary anhydrous bases include sodium methyl silyloxide, sodium triethyl silyloxide, potassium trimethyl silyloxide, potassium triethyl silyloxide, sodium triisopropyl silyloxide, sodium triisobutyl silyloxide, lithium trimethyl silyloxide and lithium triethyl silyloxide; sodium methoxide, sodium ethoxide, potassium methoxide, potassium ethoxide, sodium isopropoxide, sodium isobutoxide, lithium methoxide and lithium ethoxide.

The reaction time is not critical. The reaction is continued until the desired silyloxide product is formed. The reaction is normally rapid, and even at room temperature may need as little as ten minutes up to several hours, but it is not necessary to carry the reaction beyond a five hour reaction time. Usually, reaction is complete within from one-half to three hours.

The reaction can proceed quite rapidly at room temperature, and if it does, it very likely will also proceed at temperatures well below room temperature, down to −30° C., but there is no reason to incur the additional expense of cooling the reaction mixture. The upper limit on reaction temperature is imposed by the volatility of the reaction mixture or any component thereof, and their decomposition temperature. There is no reason to use a temperature above the boiling point of the reaction mixture at atmospheric pressure, but if the boiling temperature is too low, as, for example, in the case of methanol, a closed reaction vessel or pressurized system can be used. The reaction temperature need not exceed 200° C., taking the above factors into consideration.

The amount of silanol is at least the stoichiometric amount required to react with the ceric alkoxide and displace the desired number of alkoxy groups, from one to all, as desired. Larger than stoichiometric amounts can be used, of course, such as when the silanol is also to function as a solvent, according to the dilution of the reaction mixture required.

The ceric hydrocarbyl silyloxide is normally insoluble in the reaction mixture and can be separated during work-up by filtration. If the silyloxide is soluble in the reaction mixture, the solvent present in the reaction mixture can be removed by distillation.

The following Examples represent preferred embodiments of the invention.

In all of these Examples, the manipulations were carried out with the exclusion of oxygen and moisture, either in a $N_2$-filled, recirculating glove box (VAC, Vacuum Atmospheres Company, USA) or by the usual Schlenk technique, using argon as an inert gas. The anhydrous solvents (dimethoxyethane (DME), diethylether, THF and acetonitrile) were used as purchased in sure seal bottles without further purification. The silanols $Ph_3SiOH$, $Et_3SiOH$, $Ph_2Si(OH)_2$ were used without further purification as purchased. Ceric isopropoxide trimethyl silanol and tetramethyl disoloxanol were prepared according to the published methods.

H and C NMR spectra were recorded on a JEOL FX 90 Q FT NMR spectrometer. The solutions of the samples were prepared inside the glove box. The deuterated solvents $CHCl_3$-d, $C_6H_6$-d$_6$ and THF-d$_8$ were purchased.

EXAMPLE 1

Preparation of cerium (IV) tetra(triphenyl siloxane)

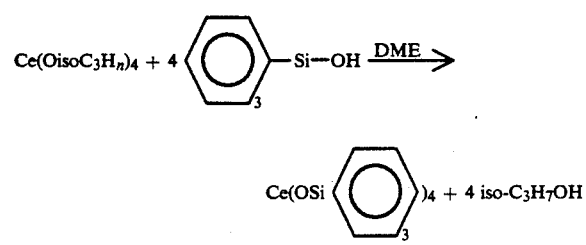

5 g of ceric isopropoxide (0.0132 mole) was dissolved in 60 ml ($\triangleq$52 g) of dimethoxyethane (DME). To the clear yellow solution 14.6 g (0.0531 mole) of triphenylsilanol was added as a solid. The $Ph_3SiOH$ went immediately into solution. After 45 minutes a white precipitate had been formed and 50 ml of ether was added and stirring was continued for the next three hours. The precipitate was then filtered using a Schlenk frit and washed with three portions of each 10 ml of diethylether. The product was dried at 1 torr and at room temperature to yield 9.8 g (60%) of a fine white powder, fairly air stable. m.p.>250° C. (dec.).

Soluble in $C_6H_6$, $CHCl_3$, acetone, glacial acetic acid, THF; slightly soluble in ether and DME, insoluble in $H_2O$.

NMR results: $^1H$ ($C_6H_6$-d$_6$)$\delta$2.9; 3.0; and 6.9; 7.0; 7.1; 7.77; 7.86; 7.87 phenyl groups as a multiplett. $^1H$ ($CHCl_3$-d)$\delta$3.0; 3.2; 6.9; 7.0; 7.1; 7.2; 7.5; 7.6. $^{13}C$ ($CHCl_3$-d)$\delta$60.24; 71.83; and 127.41; 128.83; 135.27; 138.47 phenyl groups. $^{13}C$ ($C_6H_6$-d$_6$)$\delta$59.8; 72.05; 126.9; 127.9; 129.3; 135.8; 139.0.

Elemental analyses: Calculated for $C_{72}H_{60}O_4Si_4$Ce(1240.46). C69, 65(69.20); H 4.83 (4.73); Si 9.05 (9.15); Ce 11.29 (11.22) in ( ) found values.

EXAMPLE 2

Preparation of cerium (IV) tetra(triphenyl-siloxane)

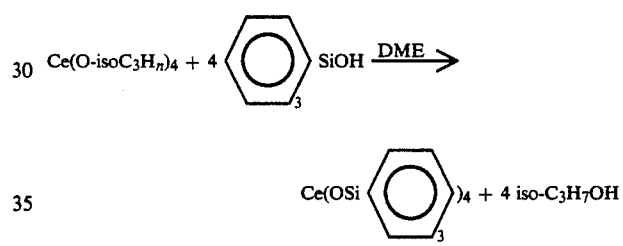

16 g of ceric isopropoxide (0.042 mole) was dissolved in 50 ml ($\triangleq$43 g) of DME. To the stirred solution, the clear colorless solution of 46.97 g (0.16 g mole) of triphenyl silanol in 50 ml (43 g) DME was added slowly via a syringe. After 10 seconds a white precipitate had been formed and stirring was continued in the next 15 minutes. The precipitate was then filtered using a Schlenk frit and washed with two portions of each 50 ml of diethylether. The product was dried at room temperature to yield 50 g of a fine white powder (96%).

Properties like solubility, m.p. and air stability are identical with those of the product described in Example 1.

NMR results: $^1H$ ($CHCl_3$-d)$\delta$3.07; 3.29; 6.87; 6.95; 7.03; 7.11; 7.19; 7.52; 7.60. $^{29}Si$($C_6H_6$-d$_6$/THF/TMS)$\delta$24.14.

EXAMPLE 3

Preparation of cerium (IV) tetra(triphenyl-siloxane)

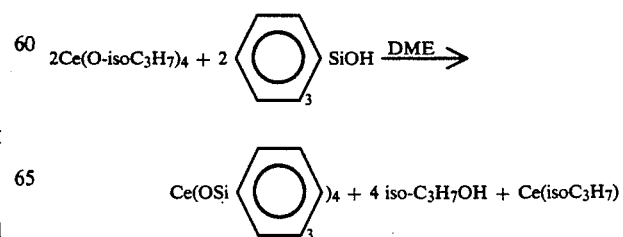

3.84 g of ceric isopropoxide (0.01019 mole) was dissolved in 20 ml (17 g) of DME. To the clear solution, 6 g (0.0217 mole) of triphenyl silanol was added as a solid. The triphenyl silanol went immediately into solution. No precipitate had been formed after 3 hours stirring. Stirring was continued overnight whereupon the formation of a white precipitate occurred. The product was filtered via a Schlenk frit, washed a few times with diethylether and dried at room temperature to yield a white fine powder 2.5 g (31.6%).

Soluble in $C_6H_6$, $CHCl_3$, acetone, glacial acetic acid, THF; slightly soluble in ether and DME, insoluble in $H_2O$.

NMR results: $^1H$ ($C_6H_6$-$d_6$)δ2.9; 3.0; and 6.9; 7.0; 7.1; 7.77; 7.86; 7.87 phenyl groups as a multiplett. $^1H$ ($CHCl_3$-d)δ3.0; 3.2; 6.9; 7.0; 7.1; 7.2; 7.5; 7.6. $^{13}C$ ($CHCl_3$-d)δ60.24; 71.83; and 127.41; 128.83; 135.27; 138.47 phenyl groups. $^{13}C$ ($C_6H_6$-$d_6$)δ59.8; 72.05; 126.9; 127.9; 129.3; 135.8; 139.0.

EXAMPLE 4

Preparation of cerium (IV) tetra(triethyl-siloxane)

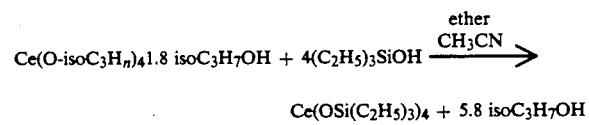

5.8 g of ceric isopropoxide ($\triangleq$0.0175 mole) was suspended in 40 ml (31 g) of acetonitrile ($CH_3CN$) and 20 ml (14 g) of diethylether was added to the suspension. A light yellow mixture formed, which contained some undissolved $Ce(OC_3H_7)_4$ 10 g of triethyl silanol (0.0757 mole) was added via a syringe. After 15 minutes stirring two layers (a greenish-yellow and a brown) had been formed and no undissolved $Ce(OisoC_3H_7)_4$ was noticed. The greenish-yellow layer was transferred to a Schlenk flask via a syringe where the solution was evaporated to dryness. A sticky bright yellow mass remained. Addition of 30 ml (23 g) $CH_3CN$ caused the formation of a milky white suspension. After stirring for 5 minutes the $CH_3CN$ was removed to yield a light yellow "wet" powder. Yield: 10 g ($\triangleq$86%).

Properties: light yellow, very hygroscopic, slightly sticky powder. Soluble in most organic solvents ($C_6H_6$, toluene, $CHCl_3$, THF, DME, ether etc.). Not soluble in $CH_3CN$. m.p.~100° C.

NMR results: $^1H$ ($CHCl_3$-d)δ0.48; 0.57; 0.65 (t, 3); 0.90; 0.98; 1.07; 1.09 (9.2). $^{13}C$ ($CHCl_3$-d)δ7.39; 7.52.

Elemental analyses: Calcd. for $C_{24}H_{60}O_4Si_4Ce$ (664.46). C 43.34 (43.47); H 9.03 (9.43); Si 16.90 (16.75); Ce 21.09 (21.10) in ( ) values found.

NMR results and elemental analyses confirm the formula $Ce(OSiEt_3)_4$

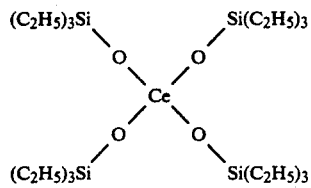

EXAMPLE 5

Preparation of cerium (IV) tetra(triethyl-siloxane)

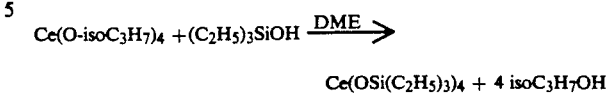

4 g (0.0106 mole) of cerium isopropoxide was dissolved in 20 ml of DME. To the stirred clear yellow solution 6 g (7 ml) of $(C_2H_5)_3$ SiOH was added via a syringe and stirring was continued for 1 hour. Then the solvent was removed at oil pump vacuum. The remaining heavy yellow oil was kept for 2 hours at 40° C. As no conversion into a powder occurred 20 ml (15 g) of $CH_3CN$ was added to form a pale yellow precipitate which was filtered using a Schlenk frit. The light yellow milky filtrate was then evaporated to dryness at oil pump vacuum to yield 4 g (57%) of a greenish/yellow wet powder.

Properties: light yellow, very hygroscopic, slightly sticky powder. Soluble in most organic solvents ($C_6H_6$, toluene, $CHCl_3$, THF, DME, ether etc.). Not soluble in $CH_3CN$. m.p.~100° C.

NMR results: $^1H$ ($CHCl_3$-d)δ0.48; 0.57; 0.65 (t, 3); 0.90; 0.98; 1.07; 1.09 (9.2). $^{13}C$ ($CHCl_3$-d)δ7.39; 7.52.

Elemental analyses: Calcd. for $C_{24}H_{60}O_4Si_4Ce$ (664.46). C 43.34 (43.47); H 9.03 (9.43); Si 16.90 (16.75); Ce 21.09 (21.10) in ( ) values found.

NMR results and elemental analyses confirm the formula $Ce(OSiEt_3)_4$

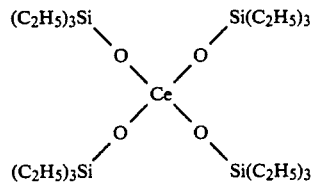

EXAMPLE 6

Preparation of cerium (IV) bis(tetramethyl-siloxydiolate)

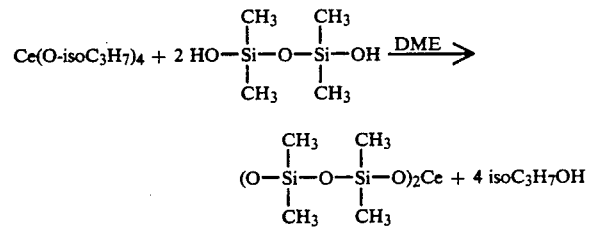

3.05 g (0.00615 mole) $Ce(iOPr)_4$ 1.8 iPrOH was dissolved in 45 ml DME. A solution of 2.05 g (0.0123 mole) of tetramethyl disiloxanol in 20 ml of DME was added to the solution causing an immediate color change from orange yellow to light yellow. After stirring for 2 hours the solvent was evaporated to dryness to yield an oily, yellow mass. In order to convert it into a powder the mass was kept for several hours at oil pump vacuum (1 torr) and upon treating with a spatula 2.8 g (97.2%) of a yellow powder was obtained as a crude product.

Further purification was obtained in the following way:

The crude product was dissolved in 20 ml of pentane and 5 ml of CH₃CN added to the clear solution. A small amount of precipitate formed immediately and the mixture was kept overnight at −30° C. A pale yellow precipitate was formed. Filtration and drying at oil pump yielded 2 g of a pale yellow powder (69%).

Properties: pale yellow, air sensitive powder; hydrophobic. Very soluble in DME, pentane, toluene; moderately soluble in CH₃CN. Dec. ~200° C.

NMR results: $^1$H (C₆H₆-d₆): δ0.342. $^{13}$C (C₆H₆-d₆): δ1.4014.

EXAMPLE 7

Preparation of cerium (IV) diisopropoxy-1,1-diphenylsilanediolate

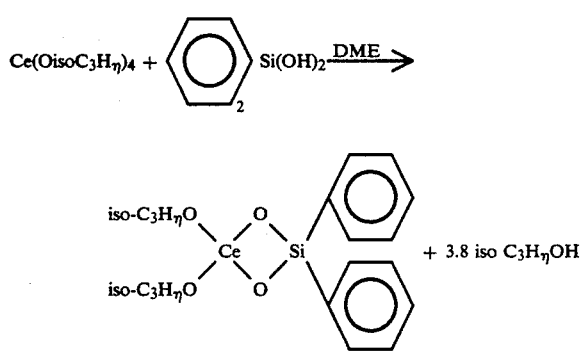

To the clear yellow solution of 6 g (0.01238 mole) Ce(OisoC₃H₇)₄ 1.8 isoC₃H₇OH in 30 ml (26 g) DME, 2.67 g (0.01238 m) of

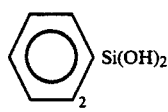

diphenylsilanediol was added as a solid. After a few minutes of stirring a thick suspension had been formed, by adding of ~10 ml of DME a clear solution was obtained, which was stirred for three hours. The solvent was removed with mild heating (~40° C.) under oil pump vacuum. Before complete drying the solid foamed up, but could be easily converted into a powder by using a spatula.

Yield: 5 g (85.5%) of a yellow, slighly air sensitive powder. Very soluble in CHCl₃, ether, DME, soluble in C₆H₆, not soluble in CH₃CN. m.p. 95°–100° C.

NMR results: $^1$H (CHCl₃-d)δ1.26; 1.33; 5.1; 7.26; 7.72. $^{13}$C (CHCl₃-d)δ27.75; 127.27; 128; 129; 134.85.

Elemental analyses: Calcd for C₁₈H₂₄O₄SiCe

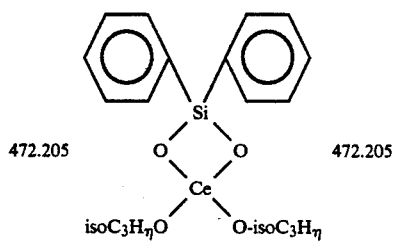

C 45.74(39.20); H 5.08(4.93); Si 5.94(6.04); Ce 29.64(30.60). Calcd for C₁₅H₂₆O₅SiCe:

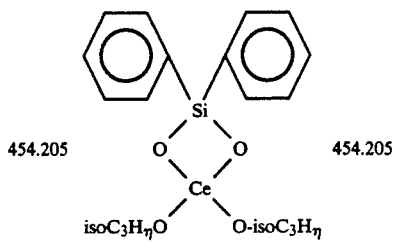

C 39.63; H 5.72; Si 6.18; Ce 30.84 in ( ) values found.

The yield of 85.5% has been based on the M.W. 472.205.

EXAMPLE 8

Preparation of cerium (IV) bis(1,4-diphenyl-silanediolate)

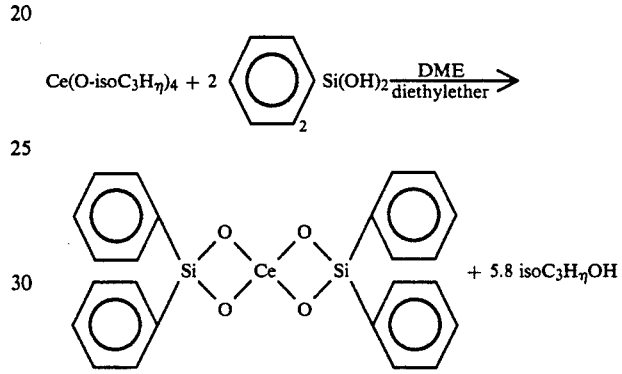

To a stirred solution of 12 g (0.02476 m) Ce(OisoC₃H₇)₄ 1.8 isoC₃H₇OH in 20 ml (14 g) of diethylether was added a solution of 10.7 g (0.0495 m) of diphenylsilanediol in 40 ml (35 g) of DME. Immediate formation of a thick, light yellow suspension occurred which made stirring almost impossible. 20 ml (14 g) of diethylether was added and stirring was continued in the next one hour. Then the reaction mixture was transferred onto a Schlenk frit and after careful filtration the yellow solid was dried on the frit to yield 11.05 g of crude product. The product was then transferred into a Schlenk flask and stirred in 48 ml (37 g) of CH₃CN for 3 hours. Subsequent filtration, drying at oil pump vacuum yielded 7.8 g of a light yellow powder: 57.3%.

Properties: Moderately air sensitive, hydrophob, light yellow powder. Soluble in THF, CHCl₃, C₆H₆, mod. soluble in DME, insoluble in CH₃CN and ether. m.p. ~155° C. (dec). Very concentrated, clear solutions in C₆H₆ or CHCl₃ freeze as glasses.

NMR results: $^1$H (C₆H₆-d₆)δ3.1; 7.15; 7.85. (CHCl₃-d)δ3.31; 7.18; 7.35; 7.55. (THF-d₈)δ3.2; 3.4; 7.16; 7.6. $^{13}$C (C₆H₆-d₆)δ126.94; 127.96; 129.10; 135.01. (CHCl₃-d)δ127.37; 128.99; 134.46.

Elemental analyses: Calcd for: C₂₄H₂₀O₄Si₂Ce (568.29)

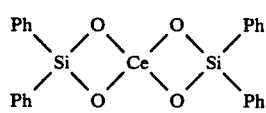

C 50.67(43.63); H 3.52(3.66); Si 9.88(10.10); Ce 24.65(25.42) in ( ) values found. Calcd for: C₂₁H₂₂O₅Si₂Ce (550.29) C 45.79; H 3.99; Si 10.21; Ce 25.46

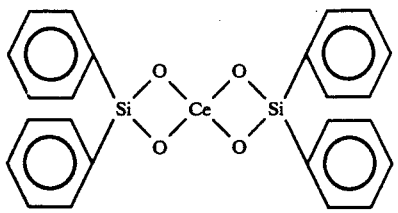

EXAMPLE 9

Reaction of Ce(O-isoC₃H₇)₄ with Ph₂Si(OH)₂ (ratio 1:4)

To a stirred solution of 4 g (0.01062 m) Ce(O-isoC₃H₇)₄ in 40 ml (35 g) of DME, 9.1 g of diphenylsilanediol (0.0424 m) was added as a solid. The diol went immediately into solution and overnight stirring of the solution caused no formation of a precipitate. The solvent was removed at oil pump vacuum. Before complete drying, a foaming sticky mass was formed, which turned into a powder after keeping it at oil pump vacuum for additional 3 hours. Yield: 8 g (78.1%).

Properties: Very light yellow, fine powder. Moderately air sensitive, hydrophobic. Well soluble in C₆H₆, CHCl₃, ether; soluble in CH₃CN, insoluble in pentane, m.p. 75°-80° C.

NMR results: ¹H (CHCl₃-d)δ3.08; 3.27; 7.14; 7.22; 7.33; 7.53; 7.61. ¹³C (CHCl₃-d)δ127.58; 127.69; 130.07; 134.41.

Elemental analyses: Calcd. for C₄₈H₄₀O₆Si₄. Ce(964.46). C 59.72 (56.86); H 4.15 (4.33); Si 11.64(10.92); Ce 14.53 (13.66) in ( ) values found.

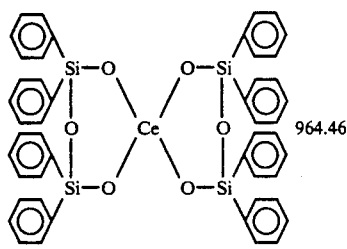

964.46

Possible structure; yield is based on this structure.

EXAMPLE 10

Reaction of Ce(O-isoC₃H₇)₄ with

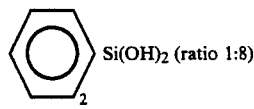

To a stirred solution of 4 g (0.00825 m) Ce(O-isoC₃H₇)₄ in 10 ml (8.6 g) DME, a solution of 15 g (0.0693 m) Ph₂Si(OH)₂ in 40 ml (35 g) was dropped slowly (total volume of Ph₂Si(OH)₂+DME was 50 ml). After the addition of 25 ml of the diol solution a light yellow suspension formed, which, however, went into solution as 35 ml of the diol had been added. After complete addition of the diol solution no formation of a precipitate was observed and stirring was continued for 2 hours. Subsequent removal of the solvent under oil pump vacuum (1 torr) left a grey/yellow oil. As no conversion into a powder was observed, the oil was kept under high vacuum (10⁻⁴ torr) for 4 hours, still not turning into a powder. However, upon keeping the oily product two days at room temperature under normal pressure, it converted into a solid cake, which on treating with a spatula could be pulverized.

Properties: grey/yellow wet powder. Fairly air stable, good soluble in toluene, DME, acetone+CHCl₃, slightly soluble in CH₃CN; insoluble in hexane m.p. 72°-74° C.

NMR results: ¹H (CHCl₃-d) δ3.15; 3.29; 7.21; 7.28; 7.43; 7.53. ¹³C (CHCl₃-d) δ127.60; 129.98; 134.32.

EXAMPLE 11

Reaction of Ce(O-isoC₃H₇)₄ with

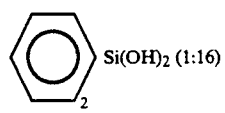

To a stirred solution of 2 g (0.00412 m) of Ce(O-isoC₃H₇)₄ 1.8 iPrOH in 40 ml (35 g) DME, 15 g of

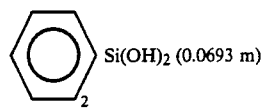

was added as a solid. After one hour of stirring an almost clear light yellow solution was formed and stirring was continued for another 3 hours. Removal of the solvent at oil pump vacuum left an oily product, which became a solid overnight at room temperature and normal pressure.

Properties: yellowish/white powder. Well soluble in toluene, acetone, CHCl₃; soluble in DME; insoluble in hexane. m.p. 97°-100° C.

NMR results: ¹H (CHCl₃-d) δ3.15; 3.29; 7.21; 7.28; 7.43; 7.53. ¹³C (CHCl₃-d) δ127.60; 129.98; 134.32.

EXAMPLE 12

Reaction of Ce(O-isoC₃H₇)₄ with

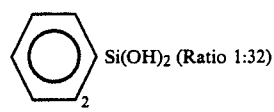

To a stirred solution of 1 g (0.00206 m) Ce(OisoC₃H₇)₄ in 20 ml (17 g) of DME, 15 g of

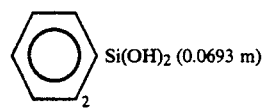

was added as a solid. A light yellow suspension was formed which did not convert into a clear solution after 45 min of stirring. Subsequent removal of the solvent with heating (~50° C.) resulted in the formation of a light yellow, almost clear heavy oil. Upon keeping the oil overnight at room temperature and under normal pressure, it turned into a solid, and was pulverized by using a spatula and dried again at oil pump vacuum.

Properties: white, almost air stable powder. Well soluble in DME, acetone, $CH_3CN$, $CHCl_3$; soluble in toluene, insoluble in hexane. m.p. 104–106.

NMR results: $^1H$ ($CHCl_3$-d) δ3.15; 3.29; 7.21; 7.28; 7.43; 7.53. $^{13}C$ ($CHCl_3$-d) δ127.60; 129.98; 134.32.

EXAMPLE 13

Preparation of cerium (IV) tetra(trimethyl siloxane)

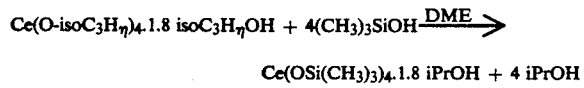

10.2 g (0.021 m) of ceric-isopropoxide was dissolved in 20 ml (17 g) of DME. To the stirred solution 9.3 ml (27.58 g ≙ 0.084 m) of trimethylsilanol was added via a syringe. After each 3 minutes a fine precipitate commenced to form and after 1 hour the reaction was regarded as complete. The precipitate was then isolated using a Schlenk frit and the yellow product was dried on the frit at oil pump vacuum. Yield: 2.7 g (26% referred to $Ce(OSiMe_3)_4$).

In a subsequent work up the dark brown red filtrate was evaporated to dryness and 5.0 g of a crude product was recovered.

NMR data: $^1H$ ($CHCl_3$-d) δ0.1362; 1.35; 1.42; 4.81. $^{13}C$ ($CHCl_3$-d) δ3.38; 25.91; 70.82.

EXAMPLE 14

Preparation of cerium (IV) bis(iso-propoxide)-bis(trimethylsiloxane)

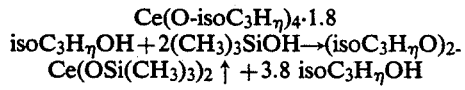

10.2 g (0.021 m) of ceric isopropoxide was dissolved in 20 ml (17 g) of DME. To the stirred solution 4.65 ml (≙ 3.79 g ≙ 0.042 m) of trimethylsilanol was added via a syringe. After each 30 minutes the red solution turned foggy and gradually a fine precipitate began to form. The mixture was allowed to react in the next four hours. Subsequent filtration via a Schlenk frit and drying at oil pump vacuum yielded 3.1 g of a pale yellow powder (33.8%).

NMR data: $^1H$ ($C_6H_6$-d$_6$) δ0.3356; 1.34; 1.41; 4.30. $^{13}C$ ($C_6H_6$-d$_6$) δ3.73; 26.37; 71.98.

EXAMPLE 15

Preparation of cerium (IV) tetramethyl siloxydiolate-di-isopropoxide

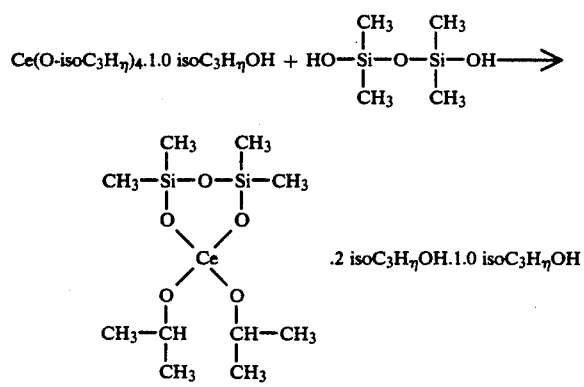

13.74 g (0.0314 m) of ceric isopropoxide and 5.25 g (0.0314 m) of tetramethyl disiloxanol were dissolved in each 10 ml of DME. Upon adding the Si-compound to the Ce-complex solution a yellow precipitate was immediately formed which partially went into solution. However, by fast filtration and drying at vacuum, it was possible to recover Ca 100 mg of yellow precipitate.

NMR data: $^1H$ ($CHCl_3$-d) δ0.0197; 1.26; 4.71. $^{13}C$ ($CHCl_3$-d) δ0.9941; 27.05; 71.80.

After the filtration a clear red filtrate was obtained which on removing the solvent turned into a heavy oil. It was not possible to convert it into a powder by further drying. Its NMR data are almost identical with those of the above mentioned yellow precipitate.

The cerium hydrocarbyl silyloxides can be employed in the manufacture of oxide powders containing cerium and silicon, useful in preparing high performance ceramics; hard gels and films containing cerium and silicon; optical fibers containing cerium and silicon polymers or oxides; additives for biocides, additives for silicone coatings such as paints, treatment of textiles and other cellulosic materials. They can also be used in various catalytic applications as for instance curing of silicone rubber, and catalysts in the manufacture of polyurethane products. The Table illustrates the potentials of some of the new compounds in a standard test demonstrating and comparing catalytic activity:

| Compound Tested | Concentration ppm | Solidification Time min. |
| --- | --- | --- |
| Nickel acetyl acetonate (a standard) | 314 | 115 |
| $Ce(O_2SiPh_2)_2$ | 260 | 105 |
| $(PrO)_2Ce—(O_2SiPh_2)$ | 320 | 105 |
| $(PrO)_2Ce—(OSiMe_3)_2$ | 372 | 45 |
| $Ce(OSiEt_3)_4$ | 233 | 80 |
| $Ce(OSiMe_3)_4$ | 282 | 69 |

The reactions were run with polyoxypropylene triol (Union Carbide's NiAX Triol LG-56) and toluene diisocyanate in a procedure described in *Journal of Applied Polymer Science*, Vol IV, No. 1, pp 207–211 (1960).

Some of the new products are surprisingly resistant to hydrolysis, while others hydrolyze very slowly. Thus it is possible to form a silyloxide having any desired rate of hydrolysis, according to the application.

Furthermore, having silicon and cerium present together in the same molecule is advantageous when both are required, as compared to adding separate cerium and silicon alkoxides.

Having regard to the foregoing disclosure, the following is claimed as the inventive and patentable embodiments thereof:

1. A process for preparing ceric hydrocarbyl silyloxides which comprises transetherifying a ceric alkoxide with a hydrocarbyl silanol having from one to three hydroxyl groups under anhydrous conditions at a temperature within the range from about −30° to about 200° C., thereby displacing at least one alkoxy group of the ceric alkoxide as aliphatic alcohol of the ceric alkoxide with a silyloxide group and forming the ceric hydrocarbyl silyloxide.

2. A process according to claim 1 in which the transetherification is carried out in solution in a solvent in which ceric hydrocarbyl silyloxide is insoluble.

3. A process according to claim 1 in which the transetherification is carried out in solution in a solvent in which ceric hydrocarbyl silyloxide is soluble.

4. A process according to claim 3, in which the solvent is the alcohol of which the ceric alkoxide is formed.

5. A process according to claim 4, which comprises separating by distillation free alcohol formed in the course of the transetherification.

6. A process according to claim 1 carried out at a reaction temperature within the range from 20° C. up to about 40° C.

7. A process according to claim 1 in which the silanol is an aliphatic silanol having from one to five carbon atoms.

8. A process according to claim 1 in which the silanol is an aliphatic, cycloaliphatic, aromatic or alkyl aromatic silanol having at least six up to about ten carbon atoms.

9. A process according to claim 8 in which the silanol is a cycloaliphatic silanol having from six to about ten carbon atoms.

10. A process according to claim 8 in which the silanol is an alkyl aromatic silanol having from seven to about ten carbon atoms.

11. A process according to claim 1 in which the silanol has the formula

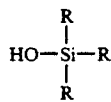

wherein:
R is a hydrocarbyl group having from one to about ten carbon atoms.

12. A process according to claim 1 in which the silanol has the formula

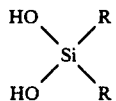

wherein:
R is a hydrocarbyl group having from one to about ten carbon atoms.

13. A process according to claim 1 in which the silanol has the formula

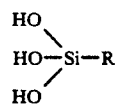

wherein:
R is a hydrocarbyl group having from one to about ten carbon atoms.

14. A process according to claim 1 in which the silanol has the formula

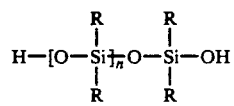

wherein:
R is a hydrocarbyl group having from one to about ten carbon atoms; and
n is the number of units in the polymer, and ranges from 2 to 100.

15. A process according to claim 1 in which the silanol has the formula

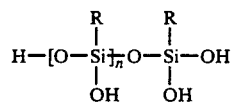

wherein:
R is a hydrocarbyl group having from one to about ten carbon atoms; and
n is the number of units in the polymer, and ranges from 2 to 100.

* * * * *